ns Patent [19]

Chin et al.

[11] Patent Number: 5,033,477
[45] Date of Patent: Jul. 23, 1991

[54] METHOD AND APPARATUS FOR PROVIDING INTRAPERICARDIAL ACCESS AND INSERTING INTRAPERICARDIAL ELECTRODES

[75] Inventors: Albert K. Chin, Palo Alto, Calif.; Thomas J. Fogarty, 5660 Alpine Rd., Portola Valley, Calif. 94028; Eric S. Fain, Menlo Park, Calif.

[73] Assignees: Thomas J. Fogarty, Portola Valley; Ventritex, Inc., Sunnyvale, both of Calif.

[21] Appl. No.: 404,957

[22] Filed: Sep. 8, 1989

Related U.S. Application Data

[63] Continuation-in-part of Ser. No. 120,590, Nov. 13, 1987, Pat. No. 4,865,037.

[51] Int. Cl.$^5$ ............................ A61N 1/05; A61N 1/39
[52] U.S. Cl. ..................... 128/785; 128/784; 128/419 D
[58] Field of Search ............... 128/419 D, 419 P, 784, 128/785, 786, 642

[56] References Cited

U.S. PATENT DOCUMENTS

| 3,866,615 | 2/1975 | Hewson | 128/419 |
|---|---|---|---|
| 4,030,509 | 6/1977 | Hellman et al. | 128/419 |
| 4,270,549 | 6/1981 | Hellman | 128/784 |
| 4,291,707 | 9/1981 | Hellman et al. | 128/784 |
| 4,548,203 | 10/1985 | Tacker, Jr. et al. | 128/419 |
| 4,567,900 | 2/1986 | Moore | 128/784 |
| 4,865,037 | 9/1989 | Chin et al. | 128/419 D |
| 4,884,567 | 12/1989 | Elliott et al. | 128/419 D |

OTHER PUBLICATIONS

"Implantation of the Automatic Defibrillator: The Subxiphoid Approach"; pp. 515 through 520; Nov. 1982; Levi Watkins, Jr., M.D. et al.

Primary Examiner—William E. Kamm
Assistant Examiner—Kennedy J. Schaetzle
Attorney, Agent, or Firm—Limbach, Limbach & Sutton

[57] ABSTRACT

Intrapericardial access is provided by clamping the wall of the pericardium between elongate jaw elements carrying axially aligned tubular guides and passing a guide wire through the guides and the pericardial tissue therebetween. In the preferred embodiment the jaw elements include interengageable ratchets for holding the elements in clamping engagement with the wall of the pericardium and aligned pointed extensions for piercing the pericardial tissue clamped between the elements. Further intrapericardial access is provided by an additional tubular guide carried by the jaw element intended to be disposed in the pericardium during placement of the guide wire.

14 Claims, 4 Drawing Sheets

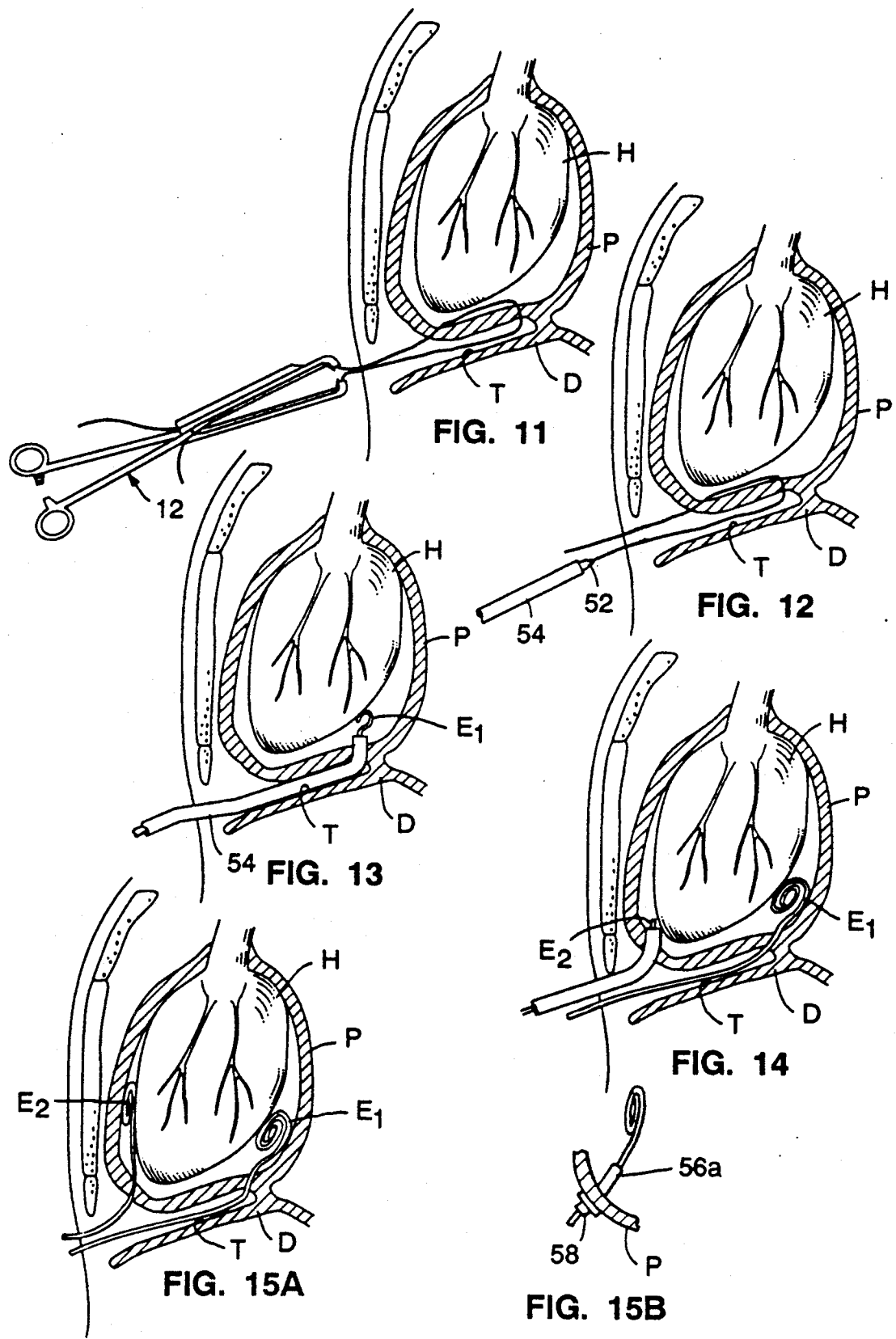

METHOD AND APPARATUS FOR PROVIDING INTRAPERICARDIAL ACCESS AND INSERTING INTRAPERICARDIAL ELECTRODES

RELATED APPLICATION

This is a continuation-in-part of copending application Ser. No. 120,590, filed Nov. 13, 1987, now U.S. Pat. No. 4,865,037.

BACKGROUND OF THE INVENTION

The present invention relates to a method and apparatus for providing intrapericardial access with a minimal amount of surgery and, more particularly, is concerned with an improved technique for extending a guide wire through the pericardial wall. In its more specific aspects, the invention is concerned with an improved method for implanting defibrillation electrodes within the pericardium.

Numerous efforts have been made to introduce implantable electrodes with a minimal amount of surgery. These efforts have affected placement both intrapericardially and extrapericardially. Where intrapericardial placement was provided, however, the prior art efforts have risked physical trauma to the heart during placement. The present invention is designed to minimize this risk.

SUMMARY OF THE INVENTION

The method of the present invention provides access to the interior of the pericardium through an incision in the inferior border of the pericardium and a tunnel dissected between the pericardium and the diaphragm. In the method, one jaw of a clamp-like placement device is extended interiorly of the pericardium through the incision and the other jaw is extended exteriorly of the pericardium through the tunnel. The jaws include tubular guide elements with aligned open distal ends curved toward one another. Once placed relative to the pericardium, the jaw elements are moved to clamp the tissue of the pericardium therebetween. A guide wire is then extended through the tubular elements and the pericardial tissue therebetween. Once the wire is so placed, the clamp-like device is removed, leaving the wire in place to facilitate access to the interior of the pericardium.

In the method of placing an electrode within the pericardium, a guide cannula is extended over the wire and into the pericardium. A primary electrode is then passed through the cannula and into the interior of the pericardium. A secondary electrode may be inserted through the incision in the inferior border of the pericardium.

The apparatus of the invention comprises the clamp-like placement device, including first and second elongate jaw elements, each of which has an open-ended tubular guide extending over the length thereof and terminating in an open distal end extending laterally of the element. It further comprises means for securing the jaw elements together in a condition wherein the open distal ends of the tubular guides are in aligned closely disposed relationship to one another. In the preferred embodiment, the apparatus further comprises means for holding the jaw elements in clamping engagement with opposite sides of pericardial tissue and a secondary open-ended tubular guide secured to and extending along at least one of the jaw elements.

A principal object of the invention is to provide a method and apparatus for accessing the interior of the pericardium with a minimum of surgery and risk of physical trauma to the heart.

Another and more specific object of the invention is to provide such a method and apparatus for extending a guide wire through the pericardial wall, without risk that the wire will effect physical trauma on the heart.

Still another object of the invention is to provide an improved method for guiding an implantable defibrillator electrode into the pericardium.

Yet another object of the invention is to provide an apparatus having a simple mode of operation which may be used to pass a guide wire into the pericardium with a minimum of surgery.

A more specific object of the invention is to provide such an apparatus having means to create a puncture through the wall of the pericardium.

A further object of the invention is to provide such an apparatus having a secondary lumen adapted to be used for the introduction of other elements into the pericardium.

These and other objects will become more apparent when viewed in light of the following detailed description and accompanying drawings.

BRIEF DESCRIPTION OF THE DRAWINGS

FIGS. 5 to 15a are cross-sectional side views of the upper region of a human body, sequentially illustrating the steps of practicing the present invention to first access the interior of the pericardium and then place defibrillator electrodes therein;

FIG. 15b is a cross-sectional elevational view, with parts thereof broken away, illustrating a modification of the arrangement shown in FIG. 15a, wherein the electrode within the anterior pericardial space is secured to the pericardium through means of a crimpable button;

DETAILED DESCRIPTION OF THE ILLUSTRATED EMBODIMENTS

Figure 1:
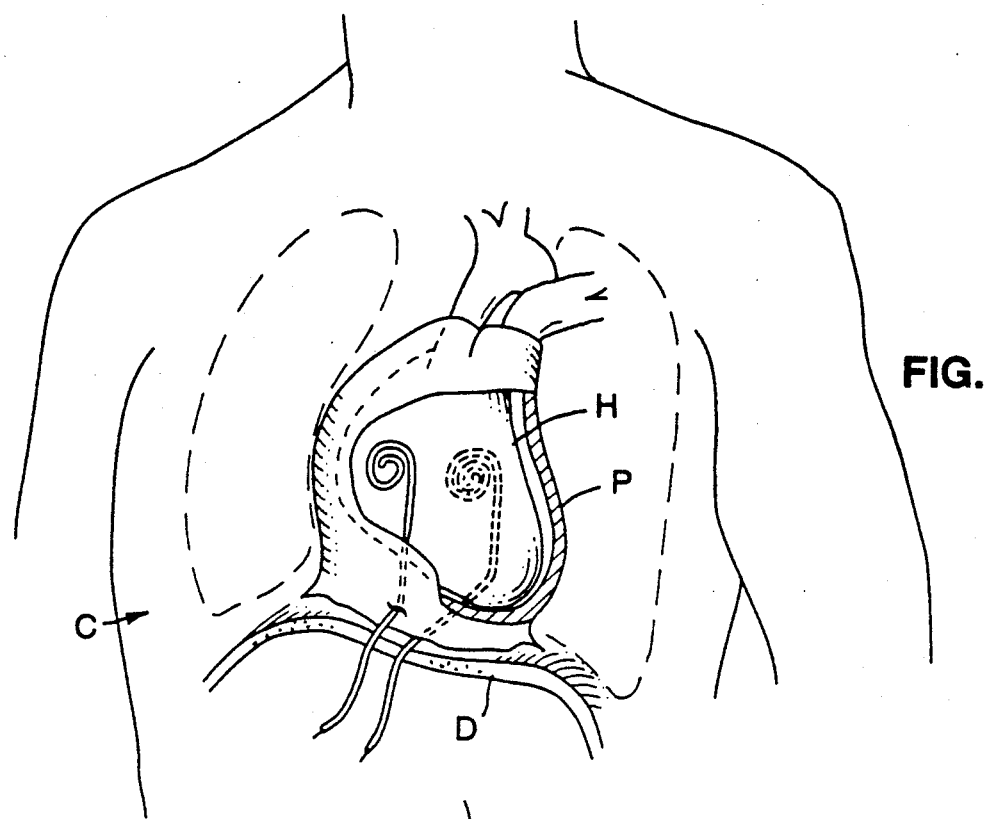
FIG. 1 is a front prospective view of the upper chest region of a human body, with parts thereof shown in section, illustrating the electrodes of a defibrillator which have been implanted in the pericardium through use of the method and apparatus of the invention.
Figure 2:
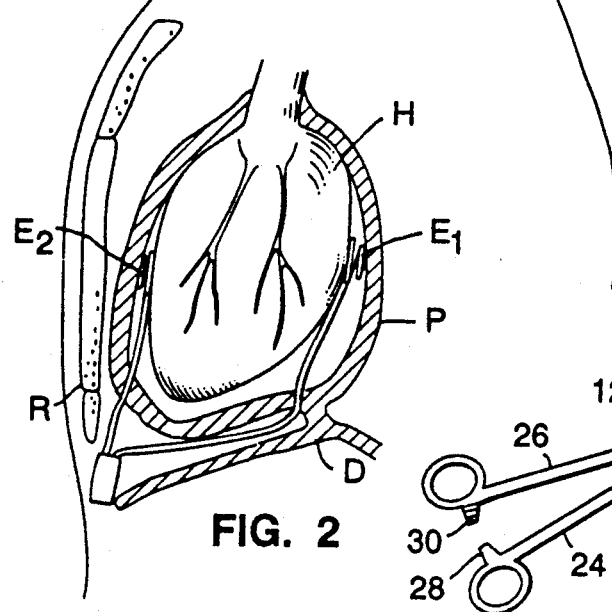
FIG. 2 is a cross-sectional side view of the body of FIG. 1.

The chest region of the human body shown in the drawings is designated in its entirety by the letter "C" and is illustrated to show the pericardium "P", the heart "H", the diaphragm "D" and the forward rib cage "R". As shown in FIGS. 1 and 2, an electrode "$E_1$" is shown posteriorly positioned within the pericardium and electrode "$E_2$" is shown anteriorly positioned within the pericardium. The electrodes "$E_1$" and "$E_2$" shown in FIGS. 1 and 2 have been placed through means of the method and apparatus of the present invention. The process for this placement is described in detail in the following discussion.

Figure 3:
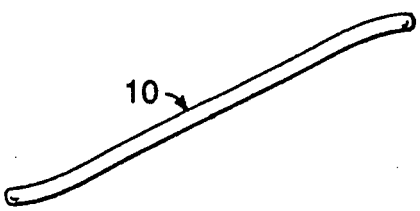
FIG. 3 is a side elevational view of a curved probe which may be used to dissect a tunnel between the pericardium and diaphragm in the method of the present invention.

The curved probe shown in FIG. 3 is designated in its entirety by the numeral 10. This probe is fabricated of a rigid material, such a stainless steel, and finished so as to have a smooth exterior surface. Its purpose, as will become more apparent from the following discussion is to enable a surgeon to dissect a tunnel between the pericardium and diaphragm through a subxiphoid incision formed in the chest wall.

Figure 4:
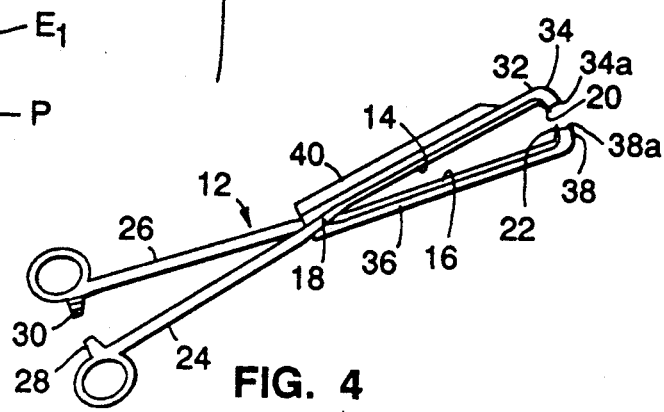
FIG. 4 is a perspective view illustrating a preferred embodiment of the intrapericardial access apparatus.

The preferred embodiment intrapericardial access apparatus of FIG. 4 is designated in its entirety by the numeral 12. This apparatus is of a forceps construction embodying upper and lower elongate jaw elements 14 and 16, respectively, similar to those used for tenaculum forceps. The jaw elements are hingedly secured together for movement toward and away from each other by a hinge pin 18. The distal ends of the jaw elements 14 and 16 are formed with rigid aligned lateral extensions 20 and 22, respectively. These extensions, as will become more apparent from the following discussion, are pointed and provided to clampingly engage the tissue of the pericardium therebetween. Handles 24 and 26 are rigidly affixed to the jaw elements 14 and 16, respectively, and terminate in thumb and finger rings. Interengageable ratchet elements 28 and 30 are formed on tee handles 24 and 26 to selectively lock the handles in a condition wherein the extensions 20 and 22 are clampingly engaged with pericardial tissue.

A first primary open-ended tubular guide 32 is fixed to and extends over the outer side of the jaw element 14 and terminates in a open distal end 34 extending laterally of the element. A second open-ended tubular guide 36 is fixed to and extends over the jaw element 16 and terminates in an open distal end 38 extending laterally of that element. The ends 34 and 38 are axially aligned when the jaw elements are clampingly engaged with the pericardial tissue and, in the preferred embodiment, are of such relative diameters that the end 38 may fit within the end 34. The edges of the ends may be sharpened to cut through the pericardial tissue upon being clamped into engagement therewith.

A secondary open-ended tubular guide 40 is fixed to and extends along the guide 32. The guide 40 terminates in a bias cut open end short of the distal end 34. The purpose of the secondary lumen is to provide additional access into the interior of the pericardium for the insertion of instruments such as: a secondary guide wire; an irrigation catheter; or a fiberoptic scope.

Figure 5:
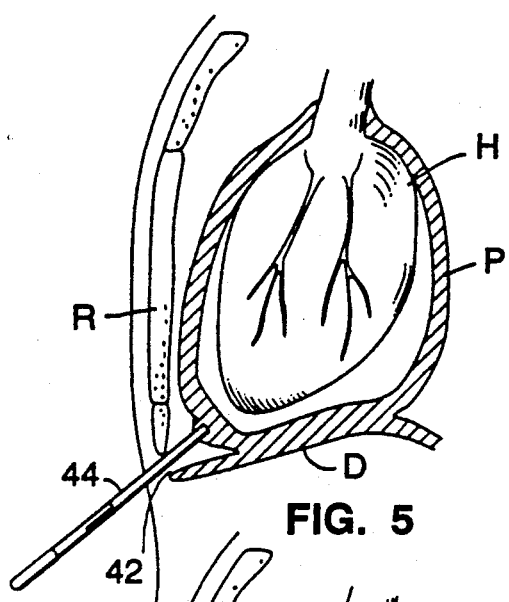

FIGS. 5 to 15a sequentially illustrate the steps of the inventive method in the process of accessing the interior of the pericardium and implanting defibrillator electrodes within the pericardium to the posterior and anterior of the heart. At the outset of the procedure, a subxiphoid incision 42 is formed in the chest wall. The method of the invention is then carried out through the following steps:

1. A pair of clamps or forceps 44 are used to pick up the inferior border of the pericardium "P" through the subxiphoid incision (FIG. 5). This is carried out under direct vision.

Figure 6:
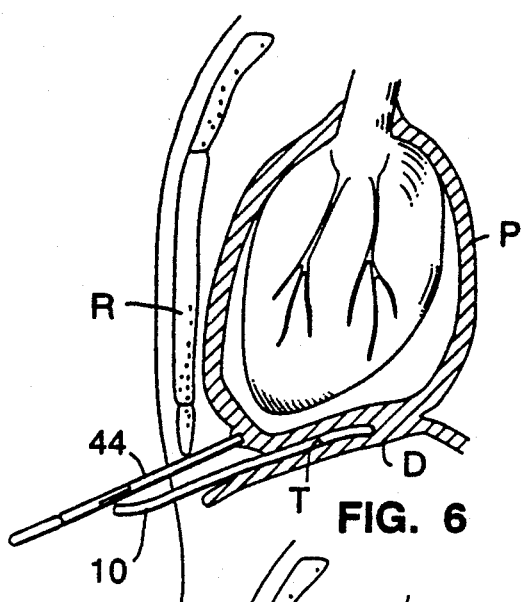

2. A curved probe, such as the probe 10 is used to dissect a tunnel "T" between the pericardium "P" and the diaphragm "D", towards the posterior aspect of the pericardium (FIG. 6). This is also carried out under direct vision, while the inferior border of the pericardium is held by the forceps 44.

Figure 7:
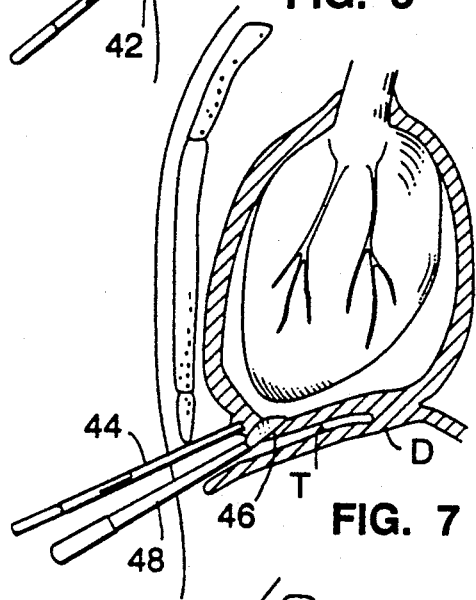

3. A small nick 46 is cut through the inferior border of the pericardium (FIG. 7). This is carried out under direct vision, using a scalpel 48 while the border of the pericardium is held with the clamp 44.

Figure 8:
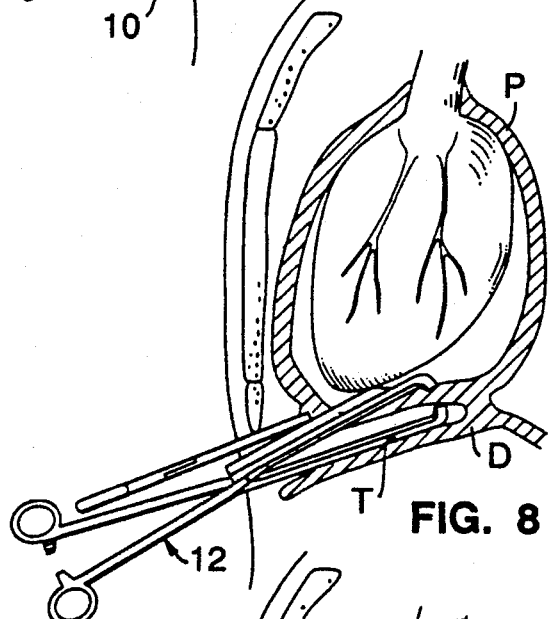

4. The intrapericardial access apparatus 12 is inserted through the incision 42 to extend the lower jaw element 16 into the tunnel "T" and the upper jaw element 14 into the pericardium through the nick 46 (FIG. 8). This step is carried out while the inferior border of the pericardium is held by the forceps 44, with the jaw elements of the apparatus 12 sufficiently spread to pass to either side of the lower wall of the pericardium.

Figure 9:
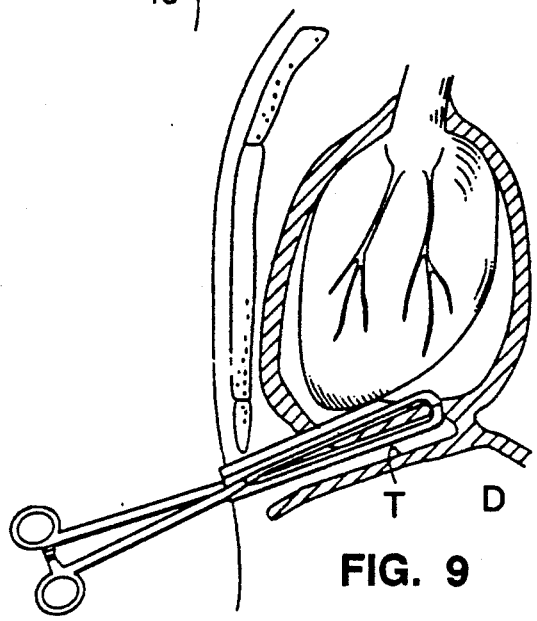

5. The jaw elements of the access apparatus are snapped together, trapping the tissue of the pericardium between them (FIG. 9). During this process, the pointed lateral extensions 20 and 22 on the elements pierce and grip surface of the tissue, thus gripping and stabilizing the apparatus relative to the pericardium. The ratchet elements 28 and 30 interengage upon snapping of the jaws together to hold the jaws in the closed condition.

Figure 10:
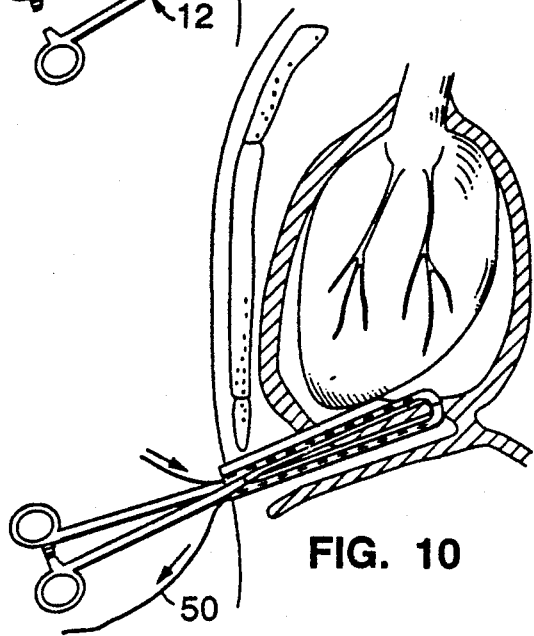

6. The next step is to pass a guide wire into the pericardium and through the lower pericardial wall (FIG. 10). Depending upon the choice of the surgeon, this may be achieved by slightly different techniques. In one, a guide wire with a sharpened tip is extended through the upper tubular guide 32 to exit therefrom and pierce through the pericardial 10 wall and pass into the lower tubular guide 36, from whence it is extended out through the subxiphoid incision. In another, after the apparatus is locked in place, it is moved back and forth to form a somewhat enlarged opening in the pericardial wall where it is pierced by the extensions 20 and 22 and then the apparatus is pulled backwards to position the distal ends of the tubular guides 36 and 38 in alignment with this hole. The guide wire, designated 50, is then extended through the inner tubular guide 32, passed through the enlarged opening, and exited out through the outer tubular guide 32. In yet another, sharpened edges $34_a$ and $38_a$ on the distal ends of the tubular guides are used to cut a hole through the pericardial wall and then the guide wire is passed from the upper tubular guide 32, through the hole and into the lower tabular guide 36. The latter technique does not require a sharpened tip on the guide wire. Regardless of which technique is used, the guide wire 50 is passed from the intrapericardial to the extrapericardial portion of the apparatus to prevent any chance of myocardial injury should the wire pass outside of the placement apparatus.

7. The intrapericardial access apparatus 12 is unsnapped and removed, leaving the guide wire 50 in place (FIG. 11). As so placed, the guide wire may be used for accessing the interior of the pericardium for any desired purpose. The steps hereinafter set forth are for the purpose of introducing defibrillation electrodes into the intrapericardial space.

8. A dilator 52 and cannula 54 are threaded over the guide wire, through the extrapericardial tunnel "T" into the intrapericardial space (FIG. 12). During this step, the dilator is first extended through the hole pierced in the lower wall of the pericardium to enlarge this hole and the cannula is then extended thereover and through the hole. Thereafter the dilator is withdrawn, leaving the cannula in place.

Figure 20:
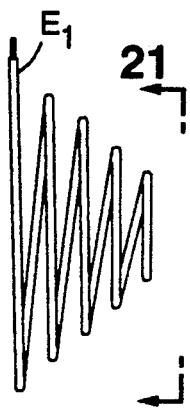
FIG. 20 is a side elevational view of a coiled electrode which may be placed through means of the method and apparatus of the present invention; and, FIG. 21 is a front elevational view of the FIG. 20 electrode, taken on the plane designated by line 21—21 of FIG. 20.
Figure 21:
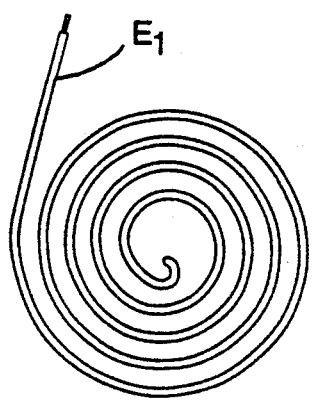

9. With the cannula 54 in place, the dilator 52 is removed and the electrode "$E_1$" is advanced through the cannula into position in the posterior intrapericardial space (FIG. 13). The electrode "$E_1$" may be of the resilient helical coil type disclosed in copending application Ser. No. 120,124, filed Nov. 12, 1987. Such electrodes are capable of being straightened into a generally rectilinear configuration to facilitate advancing them through a cannula and, when released, assume a three-dimensional helical coil configuration as may be seen in FIGS. 20 and 21 herein.

10. After the posterior electrode "$E_1$" is in place, the cannula 54 is removed and a second cannula 56 having the electrode "$E_2$" threaded therethrough is advanced into the anterior pericardial space through the inferior pericardial nick or incision 46 (FIG. 14).

11. The electrode "E" is passed through the cannula 56 to unfurl into the anterior pericardial space and the cannula 56 is then removed (FIG. 15A). The nick 46 is then closed with a suture, thus securing the electrode "$E_2$" in place. The electrode "$E_1$" is held in position by virtue of its passage through the tunnel "T" between the pericardium and the diaphragm.

As an alternative to suturing the anterior electrode "$E_2$" in place as described above, the electrode may be held in place with a crimpable annular button 58 (FIG. 15B) of the type disclosed in copending application Ser. No. 120,590. With this arrangement, a section of the second cannula, designated 56a, is left in place around the electrode "$E_2$" and the button is crimped into engagement with this section and sutured to the wall of the pericardium.

Figure 16:
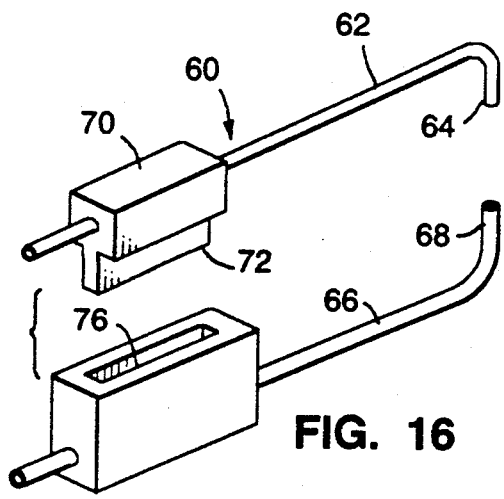
FIG. 16 is an exploded perspective view of a first alternative embodiment of the intrapericardial access apparatus.

The first alternative embodiment of the access apparatus shown in FIG. 16 is designated in its entirety by the numeral "60". This apparatus comprises: an upper jaw element 62 of an open-ended tubular configuration having an open distal end 64 extending laterally therefrom; a lower jaw element 66 of an open-ended tubular configuration having an open distal end 68 extending laterally therefrom; a T-shaped block 70 fixed to the element 62, said block including a tongue-like extension 72; and, a block 74 fixed to the jaw element 66 and having a socket 76 therein for complimental receipt of the tongue-like extension 72. The blocks 70 and 74 are so positioned relative to the elements 62 and 66 that the distal ends 64 and 68 assume an axially aligned condition when the extension 72 is received within the socket 76. The element 62 is so proportioned relative to the element 66 that the distal end 64 may be received within the distal end 66 when the extension 72 and groove 76 are complimentally engaged.

Figure 18:
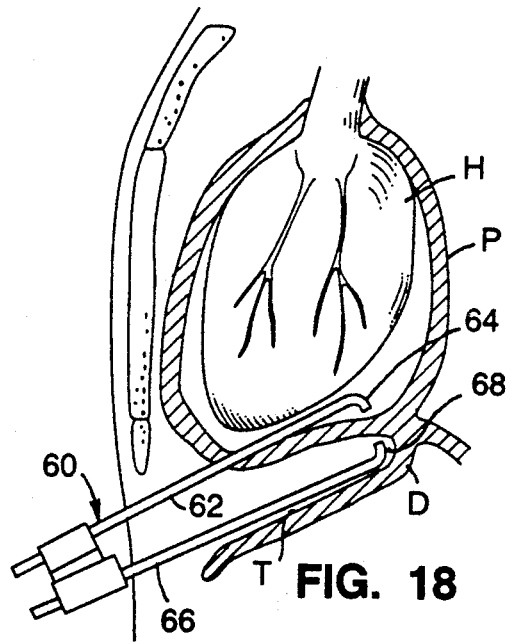
FIG. 18 is a cross-sectional view of the chest region of a human body, illustrating the first alternative embodiment access apparatus in the process of being positioned to extend to either side of the lower wall of the pericardium.
Figure 19:
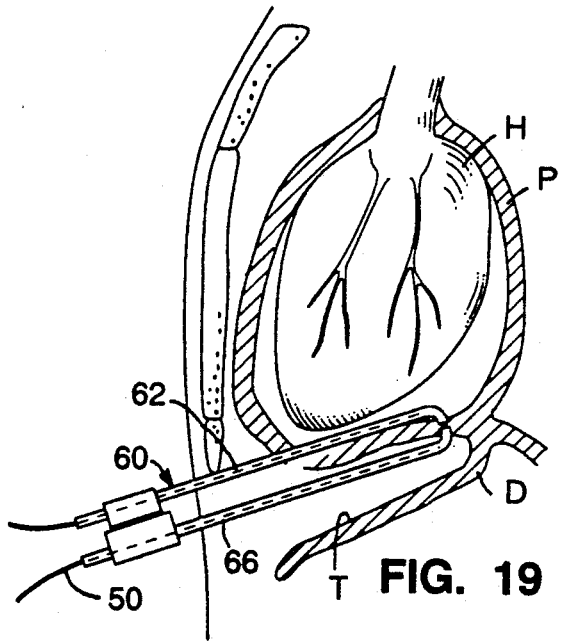
FIG. 19 is a cross-sectional elevational view similar to FIG. 18, illustrating the first alternative embodiment access apparatus in the process of being used to extend a guide wire through the lower wall of the pericardium.

The apparatus 60 is used in a manner corresponding to that of the apparatus 12, with the exception that the jaw elements of the apparatus 60 may be inserted into place individually and that the apparatus includes no pointed lateral extensions, such as the extensions 20 and 22. FIGS. 18 and 19 show the manner in which the apparatus 60 would be placed to extend a guide wire through the lower wall of the pericardium. It should be appreciated that the guide wire 50 would be provided with a sharpened tip and extended from the upper jaw element 62 through pericardium and into the lower jaw element 66.

Figure 17:
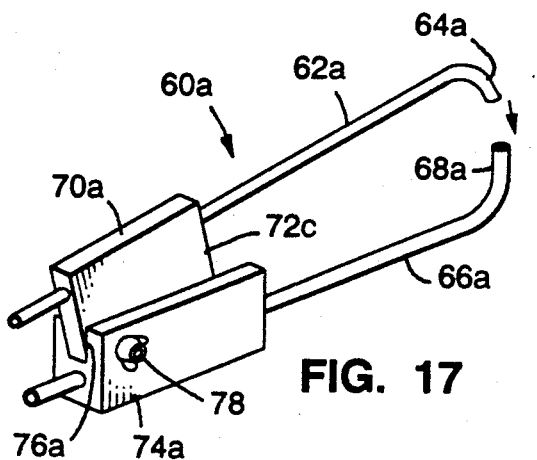
FIG. 17 is a perspective view of a second alternative embodiment of the intrapericardial access apparatus.

The second alternative embodiment apparatus of FIG. 17 is designated in its entirety by the numeral "$60_a$". The parts of the apparatus "$60_a$" are similar to those of the apparatus "60" and designated by like numerals, followed by the subscript "a" as follows: upper jaw element $62_a$; open distal end $64_a$; lower jaw element $66_a$; open distal end $68_a$; block $70_a$; tongue-like extension $72_a$; block $74_a$; and socket $76_a$. The block $70_a$ is pivotally secured to the block $74_a$ by a hinge pin 78 and is moveable about this pin between the open condition illustrated in FIG. 17 and a closed condition wherein the distal end $74_a$ is received within the distal end $68_a$.

The operation of the apparatus 60 corresponds to that of the apparatus 60, with the exception that the surgeon has the option of inserting the apparatus into place as shown in FIG. 18 with the blocks $70_a$ and $74_a$ hingedly interconnected. Alternatively, he may insert them individually and hingedly secure them together after they are in place.

CONCLUSION

From the foregoing detailed description, it is believed apparent that the present invention provides a method and apparatus whereby intrapericardial access may be provided with minimal surgery and risk of physical trauma to the heart. It should be understood, however, that the invention is not intended to be limited to the specifics of the described embodiments, but rather is defined by the accompanying claims.

We claim:

1. A method for implanting an electrode within the interior of the pericardium, comprising the steps of:
   (a) creating a subxiphoid incision;
   (b) dissecting a tunnel between the pericardium and the diaphragm from the subxiphoid incision towards the posterior aspect of the pericardium;
   (c) making a pericardial incision in the inferior border of the pericardium;
   (d) providing a clamp-like placement device having elongate tubular jaws with aligned open distal ends curved toward one another;
   (e) passing one of the jaws through the pericardial incision to locate the curved end of said one jaw at a posterior position within the pericardium;
   (f) passing the other of the jaws into the tunnel to the exterior of the pericardium to locate the curved end of said other jaw in alignment with the curved end of said one jaw;
   (g) passing a guide wire through the jaws to extend the wire within and through the pericardium;
   (h) removing the placement device while leaving the guide wire in place;
   (i) extending a cannula over the wire within the tunnel to pass the cannula through the tunnel and into the pericardium; and,
   (j) passing an electrode through the cannula and into the pericardium to one side of the heart.

2. A method according to claim 1 wherein the electrode is a first electrode and the cannula through which it is passed is a first cannula; further comprising the steps of extending a second cannula into the pericardium through the pericardial incision and passing a second electrode into the pericardium through the second cannula so as to position said second electrode on the opposite side of the heart from the first electrode 3. A method according to claim 2 further comprising the step of fastening the second electrode to the pericardium or the surrounding connective tissue to hold the second electrode in a generally fixed position within the pericardium.

4. A method according to claim 3, wherein the step of fastening the second electrode to the pericardium or the surrounding connective tissue comprises the steps of:
 (a) sliding a crimping ring over the electrode;
 (b) attaching said ring to the pericardium or the surrounding tissue; and,
 (c) crimping the ring to firmly grasp the electrode therein.

5. A method according to claim 4, wherein:
 (a) a section of the cannula is left in place between the electrode and button as the crimping ring is slid over the electrode; and,
 (b) the crimping ring is crimped onto the cannula to compress the cannula into gripping engagement with the electrode.

6. A method according to claim 1 further comprising the step of removing the guide wire after the cannula has been extended thereover.

7. A method according to claim 6 further comprising the step of removing the cannula while leaving the electrode in place within the pericardium.

8. A method according to claim 1 wherein the guide wire has a sharpened tip and is passed first through said one jaw to pierce the pericardium and then enter into and pass through said other jaw.

9. A method according to claim 1 wherein:
 (a) the elongate jaws of the placement device include aligned distal end portions capable of clamping the pericardium therebetween and forming a puncture in the pericardium;
 (b) after the jaws are passed into place said aligned distal end portions are clamped on the pericardium to form a puncture therein; and,
 (c) after the puncture is formed the placement device is moved to align the distal ends of the tubular jaws with the puncture and the guide wire is then passed through the jaws and passes through the puncture to extend through the pericardium.

10. A method according to claim 1, wherein:
 (a) the open distal ends of the tubular jaws are sharpened;
 (b) after the jaws are passed into place said open distal ends are clamped on the pericardium to cut a hole therethrough; and,
 (c) after the hole is formed the guide wire is passed through the jaws and passes through the hole to extend through the pericardium.

11. A method for accessing the interior of the pericardium, comprising the steps of:
 (a) creating a subxiphoid incision;
 (b) dissecting a tunnel between the pericardium and the diaphragm from the subxiphoid incision towards the posterior aspect of the pericardium;
 (c) making a pericardial incision in the inferior border of the pericardium;
 (d) providing a clamp-like placement device having elongate tubular jaws with aligned open distal ends curved toward one another;
 (e) passing one of the jaws through the pericardial incision to locate the curved end of said one jaw within the pericardium proximate to and interior surface thereof;
 (f) passing the other of the jaws into the tunnel to the exterior of the pericardium to locate the curved end of said other jaw proximate to an exterior surface of the pericardium in alignment with the curved end of said one jaw;
 (g) passing a guide wire through the jaws to extend the wire within and through the pericardium; and,
 (h) removing the placement device while leaving the guide wire in place.

12. A method according to claim 11 wherein the guide wire has a sharpened tip and is passed first through said one jaw to pierce the pericardium and then enter into and pass through said other jaw.

13. A method according to claim 11 wherein:
 (d) the elongate jaws of the placement device include aligned distal end portions capable of clamping the pericardium therebetween and forming a puncture in the pericardium;
 (a) after the jaws are passed into place said aligned distal end portions are clamped on the pericardium to form a puncture therein; and,
 (b) after the puncture is formed the placement device is moved to align the distal ends of the tubular jaws with the puncture and the guide wire is then passed through the jaws and passes through the puncture to extend through the pericardium.

14. A method according to claim 11, wherein:
 (a) the open distal ends of the tubular jaws are sharpened;
 (b) after the jaws are passed into place said open distal ends are clamped on the pericardium to cut a hole therethrough; and,
 (c) after the hole is formed the guide wire is passed through the jaws and passes through the hole to extend through the pericardium.

* * * * *